(12) United States Patent
Farbstein et al.

(10) Patent No.: US 12,213,990 B2
(45) Date of Patent: Feb. 4, 2025

(54) A3 ADENOSINE RECEPTOR LIGAND FOR USE FOR ACHIEVING A FAT LOSS EFFECT

(71) Applicant: CAN-FITE BIOPHARMA LTD., Petach Tikva (IL)

(72) Inventors: Motti Farbstein, Petach Tikva (IL); Inbal Itzhak, Kfar Saba (IL); Shira Cohen, Hod Hasharon (IL); Pnina Fishman, Herzliya (IL)

(73) Assignee: CAN-FITE BIOPHARMA LTD., Petach Tikva (IL)

( * ) Notice: Subject to any disclaimer, the term of this patent is extended or adjusted under 35 U.S.C. 154(b) by 812 days.

(21) Appl. No.: 17/309,952

(22) PCT Filed: Jan. 5, 2020

(86) PCT No.: PCT/IL2020/050011
§ 371 (c)(1),
(2) Date: Jul. 2, 2021

(87) PCT Pub. No.: WO2020/141535
PCT Pub. Date: Jul. 9, 2020

(65) Prior Publication Data
US 2022/0079968 A1    Mar. 17, 2022

(30) Foreign Application Priority Data
Jan. 6, 2019 (IL) .......................................... 264112

(51) Int. Cl.
*A61K 31/7076* (2006.01)
*A61K 31/4745* (2006.01)
*A61P 3/04* (2006.01)

(52) U.S. Cl.
CPC ...... *A61K 31/7076* (2013.01); *A61K 31/4745* (2013.01); *A61P 3/04* (2018.01)

(58) Field of Classification Search
CPC ............ A61K 31/4706; A61K 31/4745; A61K 31/7076; A61P 3/04; A61P 3/06
See application file for complete search history.

(56) References Cited

U.S. PATENT DOCUMENTS

2018/0264022 A1* 9/2018 Fishman ................... A61P 1/16

FOREIGN PATENT DOCUMENTS

| CN | 108367016 A | 8/2018 |
| KR | 10-1881441 B1 | 7/2018 |
| WO | 2004/007519 A1 | 1/2004 |
| WO | 2013/111132 A1 | 8/2013 |
| WO | 2017/090036 A1 | 6/2017 |

OTHER PUBLICATIONS

Jeong (KR101881441B1; machine English translation done on Jun. 18, 2024).*
Rasouli et al., "Ectopic fat accumulation and metabolic syndrome", Diabetes Obes Metab, 2007, vol. 9, No. 1, pp. 1-10.
Nigro et al., "New Insight into Adiponectin Role in Obesity and Obesity-Related Diseases", BioMed Research International, 2014, vol. 2014, Article ID 658913, 14 pages.
Okamura et al., "Ectopic fat obesity presents the greatest risk for incident type 2 diabetes: a population-based longitudinal study", International Journal of Obesity, 43: 139-148 (2019).

* cited by examiner

*Primary Examiner* — Pancham Bakshi
(74) *Attorney, Agent, or Firm* — Vorys, Sater, Seymour, and Pease LLP; Anthony P. Venturino; Maryellen Feehery Hank

(57) ABSTRACT

Provided is an A3 adenosine receptor ($A_3AR$) ligand for use in achieving at least one fat loss effect selected from: reducing weight of the subject; reducing body fat mass in the subject; treating obesity in the subject and inhibiting adipocytes proliferation in a subject. The disclosure also concerns pharmaceutical compositions, methods of treatment and kits comprising the $A_3AR$ ligand.

5 Claims, 3 Drawing Sheets

A3 ADENOSINE RECEPTOR LIGAND FOR USE FOR ACHIEVING A FAT LOSS EFFECT

TECHNOLOGICAL FIELD

The present disclosure concerns medical uses of $A_3AR$ ligands.

BACKGROUND ART

References considered to be relevant as background to the presently disclosed subject matter are listed below:
   International Patent Application Publication No. WO04/007519
   International Patent Application Publication No. WO2013/111132
   International Patent Application Publication No. WO/17090036

Acknowledgement of the above references herein is not to be inferred as meaning that these are in any way relevant to the patentability of the presently disclosed subject matter.

BACKGROUND

Obesity is a complex disease involving an excessive amount of body fat that is considered to be a major health, at times life threatening concern in Western societies.

Obesity results from an imbalance of food intake, basal metabolism, and energy expenditure. At an individual level, multiple endogenous or environmental causes could lead to obesity. However, in most cases, a combination of excessive caloric intake and availability of energy-dense meals is thought to be the main contributor to obesity.

While weight loss can improve or prevent the health issues associated obesity, there are situations where there is a need to combine weight loss procedures with medication.

International patent application publication No. WO04/007519 describes compounds that are partial or full Al adenosine receptor agonists, and to their use in treating mammals for various disease states, including diabetic disorders, obesity, and modifying adipocyte function.

International Patent Application Publication No. WO2013/111132 describes the use of 2-Chloro-$N^6$-(3-iodobenzyl)-adenosine-5'-N-methyluronamide (Cl-IB-IMECA, CF102) Cl-IB-MECA for treatment of hepatocellular carcinoma (HCC) and for maintaining liver function in a subject having a chronic liver disease.

International Patent Application Publication No. WO17/090036 describes the use of $A_3AR$ ligands, specifically, Cl-IB-IMECA, for reducing ectopic fat accumulation, particularly in fatty liver, and specifically, for treating non-alcoholic fatty liver disease (NAFLD).

GENERAL DESCRIPTION

The present disclosure provides, in accordance with a first of its aspects, an $A_3$ adenosine receptor ($A_3AR$) ligand for use in any one of the following indications:
   reducing weight of a subject;
   reducing body fat mass in a subject;
   treating obesity in a subject;
   reducing level of adipocytes in a subject; and
   inhibiting adipocytes proliferation in a subject.

The present disclosure provides, in accordance with a second aspect, a pharmaceutical composition comprising as active ingredient an $A_3AR$ ligand in an amount effective to achieve at least one fat loss effect selected from:
   reducing weight of a subject;
   reducing body fat mass in a subject;
   treating obesity in a subject;
   reducing level of adipocytes in a subject; and
   inhibiting adipocytes proliferation in a subject.

Also provided by the present disclosure, is a method of treatment, the method comprising administering to a subject in need an amount of an $A_3AR$ ligand, the amount being effective to achieve at least one fat loss effect selected from:
   reducing weight of a subject;
   reducing body fat mass in a subject;
   treating obesity in a subject;
   reducing level of adipocytes in a subject;
   inhibiting adipocytes proliferation in a subject.

In some examples, the $A_3AR$ ligand is an the $A_3AR$ agonist, preferably 2-chloro-$N^6$-(3-iodobenzyl)-adenosine-5'-N-methyluronamide (Cl-IB-MECA, herein also referred to as CF102).

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 2A-2B are microscopic images showing accumulation of lipid droplets produced by 3T3-L1 adipocytes.

DETAILED DESCRIPTION

The present disclosure is based on the finding that 2-chloro-$N^6$-(3-iodobenzyl)-adenosine-5'-N-methyluronamide (CL-IB-MECA, herein also referred to as CF102), an $A_3$ adenosine receptor ($A_3AR$) agonist, with high affinity and selectivity to the $A_3AR$, inhibited proliferation of adipocytes in an in-vitro adipocytes proliferation model.

Figure 1:
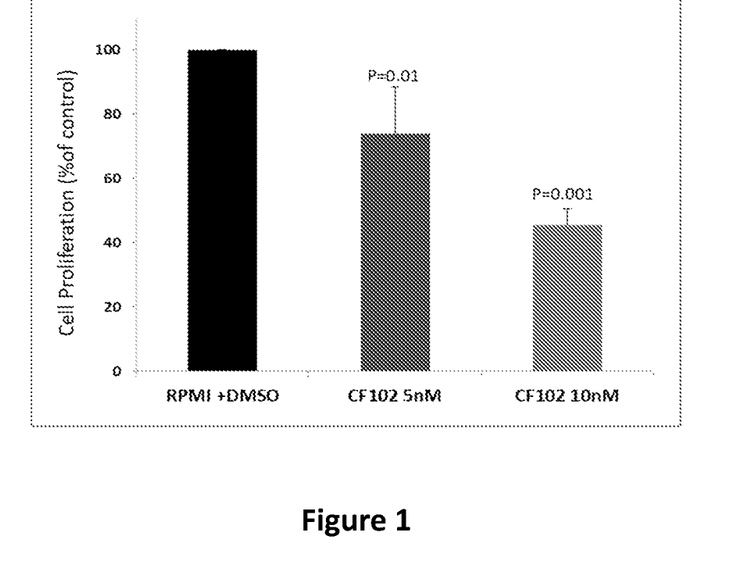
FIG. 1 is a bar graph showing s dose dependent inhibition of adipocyte cells proliferation using two doses of Cl-IB-IMECA (CF102), with respect to a control group (RPMI+DMSO).
Figure 2A:
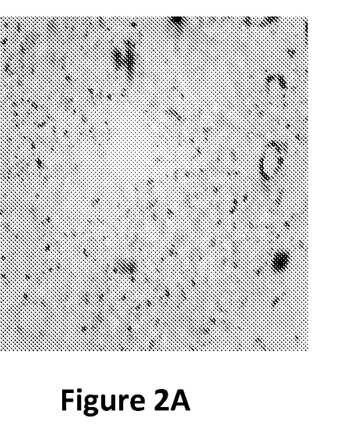
FIG. 2A shows accumulation following treatment with vehicle only)
Figure 2B:
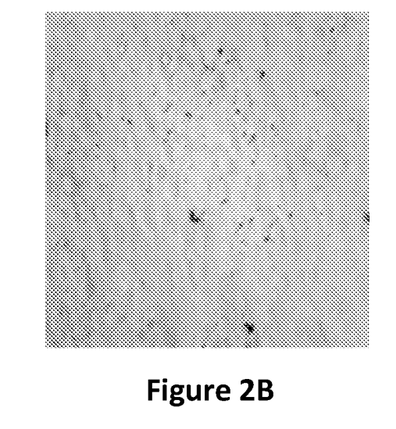
FIG. 2B showing level of accumulation following treatment of the cells with 5 nM of Cl-IB-MECA.
Figure 3:
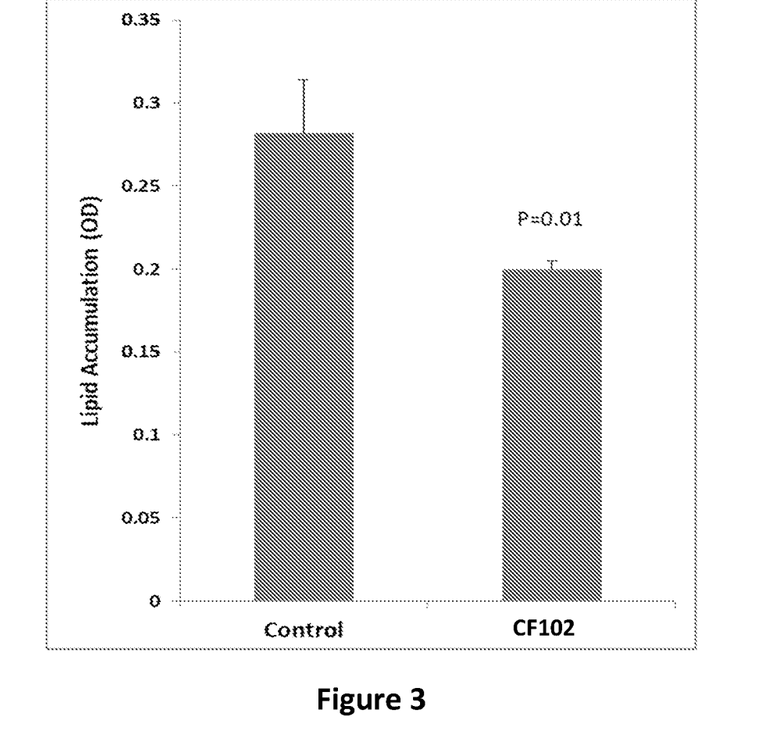
FIG. 3 is bar graph showing optical density of lipid droplets accumulation produced by 3T3-L1 adipocytes following treatment of 3T3-L1 adipocytes with 5 nM of Cl-IB-MECA compared to a control group (DMEM high glucose+10% FBS).

This unexpected inhibition was exhibited, inter alia, by the reduction of level of adipocytes (FIG. 1) and by the reduction of lipid accumulation produced by 3T3-L1 adipocytes (FIGS. 2A-2B and 3).

In addition, the unexpected effect of Cl-IB-MECA was exhibited in a statistically significant weight loss of high fat diet mice.

Further, unexpectedly, the weight loss was also exhibited in an animal model for diabetics, which is a known complication of obesity upon treatment with an $A_3AR$ allosteric modulator N-(3,4-Dichloro-phenyl)-2-cyclohexyl-1H-imidazo[4,5-c]quinolin-4-amine (referred to at times by the abbreviation LUF6000 or CF602).

Based on these findings, it has been concluded by the inventors that a ligand with high affinity and selectivity to the $A_3AR$, be it an $A_3AR$ selective agonist or an $A_3AR$ selective allosteric modulator, is an effective tool for achieving a therapeutically beneficiary effect in any one or combination of the following:

reducing weight of a subject;
reducing body fat mass in a subject;
treating obesity in a subject;
reducing level of adipocytes in a subject; and
inhibiting adipocytes proliferation in a subject.

Without being bound by theory, the above effects are considered to be linked together, directly or indirectly by the inhibitory effect the ligand has on the proliferation of adipocytes and thus, are collectedly referred to as the "fat loss effects".

In the context of the present disclosure, each of the above effects or any combination of two or more such effects is to be considered as a separate embodiment.

Thus, the present disclosure provides an $A_3AR$ ligand for use in achieving any of the above fat loss effects, as well as pharmaceutical compositions comprising the $A_3AR$ ligand for use in achieving any of the above fat loss effects and methods of treatment of a subject in need of any one of the above fat loss effects; the treatment also encompassing prevention of gaining fat, as further discussed below.

In one example, the $A_3AR$ ligand is for use in treating a subject suffering from obesity.

In one other example, the $A_3AR$ ligand is for use in inducing or promoting weight loss in a subject.

In yet one other example, the $A_3AR$ ligand is for use in reducing level of adipocytes in a subject.

In yet one further example, the $A_3AR$ ligand is for inhibiting proliferation of adipocytes.

In the context of the present disclosure, when referring to weight loss or treatment of obesity it is to be understood as equivalently referring to reducing fatty tissues, such as adipose tissues that are intended to store fat, namely subcutaneous and/or peripheral fat, and excluding ectopic fat, such as ectopic fat in a liver tissue. In some examples, the present disclosure excludes reduction of ectopic fatty tissue, and specifically fatty tissue in the liver.

In one preferred example, the $A_3AR$ ligand is used for treating a subject having excess of body fat, particularly a subject suffering from obesity.

In some examples, the reduction of body fat mass is exhibited by a reduction of peripheral fat, in particular reduction of adipose tissues.

In some other examples, the reduction of body fat mass is exhibited by reduction of lipid production of 3T3-L1 adipocytes.

Excess of body fat may be determined according to the Body Mass Index (BMI). A subject having a BMI over 25 is considered to have excess body fat, and above BMI of 30 it is considered that the subject suffers from obesity.

The effect of treatment, e.g. the reduction of the measurands according to the present disclosure, e.g. weight, body fat mass and/or level of adipocytes, can be determined by their values taken in two different time points. In some examples, the first time point is before treatment has begun and the second time point is during treatment.

In some examples, the two time points is during treatment. The time difference between the first time point and the second time point may be, for example, a day, a week, a month and even up to a year, wherein in between the subject is being given the $A_3AR$ ligand according to any of the embodiments of the present disclosure.

When referring to a reduction of a value of one of the measurands, it is to be understood that the reduction of the value is to any extent that is considered by the physician as significant. It can be by 1% as compared to a predetermined reference time point, 5%, 10%, 15%, 20%, 25%, 30%, 40%, 50%, 60% or at times above 70%. It is to be noted that between a reference time point and an evaluation time point there may be a plurality of time points in which measurements of the value are taken.

In some examples, the reference time point is before treatment has begun. In some other examples, the reference time point is a point during treatment.

In some examples, the evaluation time point is a time point determined to be the end of treatment. In some other examples, the evaluation time point is a point during treatment that is subsequent to the reference time point.

It is to be noted that between the two time points the subject is being given the $A_3AR$ ligand. However, treatment with the $A_3AR$ ligand does not need to be chronic, e.g. during the entire period and it may be that the subject is given periodically.

In one example, the treatment with the $A_3AR$ ligand is chronic treatment, namely, during the entire treatment period.

In the context of the present disclosure "$A_3$ adenosine receptor ligand" or "$A_3AR$ ligand" denotes any compound that directly (e.g. via the receptor binding site) or indirectly (e.g. via an allosteric binding site) affects the activity of the $A_3$ adenosine receptor, this including full or partial activation of the $A_3$ adenosine receptor.

The $A_3AR$ ligand according to the present disclosure is a molecule that exerts its prime effect through the activity of the $A_3AR$ irrespective of whether the activation is via the binding site or allosteric binding site.

The $A_3AR$ ligand has high affinity and selectivity to the $A_3AR$. This means that at the doses it is being administered it essentially affects only the $A_3AR$.

The specificity and high affinity of the ligand to the $A_3$ adenosine receptor provides a beneficial effect over activation of the other adenosine receptors, such as the $A_1$ adenosine receptor, known to have, inter alia, cardiovascular side effects that are absent when using an $A_3AR$ ligand. In fact, researches have shown that $A_3AR$ ligand have a protective effect, inter alia, neuroprotective effect, chemoprotective effect, cardioprotective effect, and hepatoprotective effect.

In one example, the "$A_3$ adenosine receptor ligand" is an $A_3AR$ agonist.

In one other example, the "$A_3$ adenosine receptor ligand" is an $A_3AR$ allosteric modulator (can also be termed allosteric effector).

When referring to "$A_3$ adenosine receptor agonist" or "$A_3AR$ agonist" it is to be understood to mean any ligand capable of specifically binding to the $A_3$ adenosine receptor, thereby fully or partially activating the $A_3$ adenosine receptor.

A molecule will be considered an $A_3AR$ agonist in the context of the present disclosure (namely a molecule that exerts its prime effect through the binding and activation $A_3AR$) if its affinity to the $A_3AR$ is at least 3 times (i.e. its Ki to the $A_3AR$ is at least 3 times lower), preferably 10 times, desirably 20 times and most preferably at least 50 times larger than the affinity to any other of the adenosine receptors (i.e. $A_1$, $A_{2a}$ and $A_{2b}$).

The affinity of an $A_3AR$ agonist to the human $A_3AR$ as well as its relative affinity to the other human adenosine receptors can be determined by a number of assays, such as a binding assay. Examples of binding assays include providing membranes containing a receptor and measuring the ability of the $A_3AR$ agonist to displace a bound radioactive agonist; utilizing cells that display the respective human adenosine receptor and measuring, in a functional assay, the ability of the $A_3AR$ agonist to activate or deactivate, as the case may be, downstream signaling events such as the effect on adenylate cyclase measured through increase or decrease of the cAMP level; etc. If the administered level of an $A_3AR$ agonist is increased such that its blood level reaches a level approaching that of the Ki of the $A_1$, $A_{2a}$ and $A_{2b}$ adenosine receptors, activation of these receptors may occur following such administration, in addition to activation of the $A_3AR$. An $A_3AR$ agonist is thus preferably administered at a dose such that the blood level is such so that essentially only the $A_3AR$ will be activated.

In one example, the $A_3AR$ agonist has a binding affinity (Ki) to the human $A_3AR$ in the range of less than 100 nM, typically less than 50 nM, preferably less than 20 nM, more preferably less than 10 nM and ideally less than 5 nM. Particularly preferred are $A_3AR$ agonists that have a Ki to the human $A_3R$ of less than 2 nM and desirably less than 1 nM.

In the context of the present disclosure, it should be understood that some $A_3AR$ agonists can also interact with and activate other adenosine receptors, however, with lower affinities (namely a higher Ki).

In some examples, the $A_3AR$ agonist is a molecule that has a purine backbone. The purine containing compound can be determined as an $A_3AR$ agonist based on acceptable structure-function activity assays.

The characteristic of some $A_3AR$ agonists to be used according to the present disclosure and methods of their preparation are described in detail in, inter alia, U.S. Pat. Nos. 5,688,774; 5,773,423; 5,573,772; 5,443,836; 6,048,865, WO 95/02604, WO 99/20284, WO 99/06053, WO 97/27173 and WO 01/19360, all of which are incorporated herein by reference.

According to some examples of the present disclosure, the $A_3AR$ agonist is a purine derivative falling within the scope of the general formula (I):

(I)

wherein,
$R_{11}$ represents an alkyl, hydroxyalkyl, carboxyalkyl or cyanoalkyl or a group of the following general formula (II):

(II)

in which:
Y represents oxygen, sulfur or $CH_2$;
$X_{11}$ represents H, alkyl, $R^eR^fNC(=O)—$ or $HOR^g—$, wherein
$R^e$ and $R^f$ may be the same or different and are selected from the group consisting of hydrogen, alkyl, amino, haloalkyl, aminoalkyl, BOC-aminoalkyl, and cycloalkyl or are joined together to form a heterocyclic ring containing two to five carbon atoms; and
$R^g$ is selected from the group consisting of alkyl, amino, haloalkyl, aminoalkyl, BOC-aminoalkyl, and cycloalkyl;
$X_{12}$ is H, hydroxyl, alkylamino, alkylamido or hydroxyalkyl;
$X_{13}$ and $X_{14}$ represent independently hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both $X_{13}$ and $X_{14}$ are oxygens connected to >C=S to form a 5-membered ring, or $X_{12}$ and $X_{13}$ form the ring of formula (III):

(III)

where R' and R" represent independently an alkyl group;
$R_{12}$ is selected from the group consisting of hydrogen, halo, alkylether, amino, hydrazido, alkylamino, alkoxy, thioalkoxy, pyridylthio, alkenyl; alkynyl, thio, and alkylthio; and
$R_{13}$ is a group of the formula $—NR_{15}R_{16}$ wherein
$R_{15}$ is a hydrogen atom or a group selected from alkyl, substituted alkyl or aryl-NH—C(Z)—, with Z being O, S, or $NR^a$ with $R^e$ having the above meanings; wherein when $R_{15}$ is hydrogen than
$R_{16}$ is selected from the group consisting of R- and S-1-phenylethyl, benzyl, phenylethyl or anilide groups unsubstituted or substituted in one or more positions with a substituent selected from the group consisting of alkyl, amino, halo, haloalkyl, nitro, hydroxyl, acetoamido, alkoxy, and sulfonic acid or a salt thereof, benzodioxanemethyl, fururyl, L-propylalanyl-aminobenzyl, β-alanylamino-benzyl, T-BOC-β-alanylaminobenzyl, phenylamino, carbamoyl, phenoxy or cycloalkyl; or $R_{16}$ is a group of the following formula (IV):

(IV)

or when $R_{15}$ is an alkyl or aryl-NH—C(Z)—, then, $R_{16}$ is selected from the group consisting of heteroaryl-$NR^a$—C(Z)—, heteroaryl-C(Z)—, alkaryl-$NR^a$—C(Z)—, alkaryl-C(Z)—, aryl-NR—C(Z)— and aryl-C(Z)—; Z representing an oxygen, sulfur or amine.

Exemplary A₃AR agonist (disclosed in U.S. Pat. No. 5,688,774 at column 4, lines 67-column 6, line 16; column 5, lines 40-45; column 6, lines 21-42; column 7, lines 1-11; column 7, lines 34-36; and column 7, lines 60-61):

$N^6$-(3-iodobenzyl)-9-methyladenine;
$N^6$-(3-iodobenzyl)-9-hydroxyethyladenine;
R—$N^6$-(3-iodobenzyl)-9-(2,3-dihydroxypropyl)adenine;
S—$N^6$-(3-iodobenzyl)-9-(2,3-dihydroxypropyl)adenine;
$N^6$-(3-iodobenzyladenin-9-yl)acetic acid;
$N^6$-(3-iodobenzyl)-9-(3-cyanopropyl)adenine;
2-chloro-$N^6$-(3-iodobenzyl)-9-methyladenine;
2-amino-$N^6$-(3-iodobenzyl)-9-methyladenine;
2-hydrazido-$N^6$-(3-iodobenzyl)-9-methyladenine;
$N^6$-(3-iodobenzyl)-2-methylamino-9-methyladenine;
2-dimethylamino-$N^6$-(3-iodobenzyl)-9-methyladenine;
$N^6$-(3-iodobenzyl)-9-methyl-2-propylaminoadenine;
2-hexylamino-$N^6$-(3-iodobenzyl)-9-methyladenine;
$N^6$-(3-iodobenzyl)-2-methoxy-9-methyladenine;
$N^6$-(3-iodobenzyl)-9-methyl-2-methylthioadenine;
$N^6$-(3-iodobenzyl)-9-methyl-2-(4-pyridylthio)adenine;
(1S, 2R, 3S, 4R)-4-(6-amino-2-phenylethylamino-9H-purin-9-yl)cyclopentane-1,2,3-triol;
(1S, 2R, 3S, 4R)-4-(6-amino-2-chloro-9H-purin-9-yl)cyclopentane-1,2,3-triol;
(±)-9-[2α,3α-dihydroxy-4β-(N-methylcarbamoyl)cyclopent-1β-yl)]-$N^6$-(3-iodobenzyl)-adenine;
2-chloro-9-(2'-amino-2',3'-dideoxy-β-D-5'-methyl-arabinofuronamido)-$N^6$-(3-iodobenzyl)adenine;
2-chloro-9-(2',3'-dideoxy-2'-fluoro-β-D-5'-methyl-arabino furonamido)-$N^6$-(3-iodobenzyl)adenine;
9-(2-acetyl-3-deoxy-β-D-5-methyl-ribofuronamido)-2-chloro-$N^6$-(3-iodobenzyl)adenine;
2-chloro-9-(3-deoxy-2-methanesulfonyl-β-D-5-methyl-ribofuronamido)-$N^6$-(3-iodobenzyl)adenine;
2-chloro-9-(3-deoxy-β-D-5-methyl-ribofuronamido)-$N^6$-(3-iodobenzyl)adenine;
2-chloro-9-(3,5-1,1,3,3-tetraisopropyldisiloxyl-β-D-5-ribofuranosyl)-$N^6$-(3-iodobenzyl)adenine;
2-chloro-9-(2',3'-O-thiocarbonyl-β-D-5-methyl-ribofuronamido)-$N^6$-(3-iodobenzyl)adenine;
9-(2-phenoxythiocarbonyl-3-deoxy-3-D-5-methyl-ribofuronamido)-2-chloro-$N^6$-(3-iodobenzyl)adenine;
1-(6-benzylamino-9H-purin-9-yl)-1-deoxy-N,4-dimethyl-β-D-ribofuranosiduronamide;
2-chloro-9-(2,3-dideoxy-β-D-5-methyl-ribofuronamido)-$N^6$ benzyladenine;
2-chloro-9-(2'-azido-2',3'-dideoxy-β-D-5'-methyl-arabinofuronamido)-$N^6$-benzyladenine;
2-chloro-9-(β-D-erythrofuranoside)-$N^6$-(3-iodobenzyl)adenine;
$N^6$-(benzodioxanemethyl)adenosine;
1-(6-furfurylamino-9H-purin-9-yl)-1-deoxy-N-methyl-β-D-ribofuranosiduronamide;
$N^6$-[3-(L-prolylamino)benzyl]adenosine-5'-N-methyluronamide;
$N^6$-[3-(D-alanylamino)benzyl]adenosine-5'-N-methyluronamide;
$N^6$-[3-(N-T-Boc-β-alanylamino)benzyl]adenosine-5'-N-methyluronamide
6-(N'-phenylhydrazinyl)purine-9-β-ribofuranoside-5'-N-methyluronamide;
6-(O-phenylhydroxylamino)purine-9-β-ribofuranoside-5'-N-methyluronamide;
9-(β-D-2',3'-dideoxyerythrofuranosyl)-$N^6$-[(3-β-alanylamino)benzyl]adenosine;
9-(β-D-erythrofuranoside)-2-methylamino-$N^6$-(3-iodobenzyl)adenine;

2-chloro-N-(3-iodobenzyl)-9-(2-tetrahydrofuryl)-9H-purin-6-amine;
2-chloro-(2'-deoxy-6'-thio-L-arabinosyl)adenine; and
2-chloro-(6'-thio-L-arabinosyl)adenine.

Other exemplary A₃AR agonists, disclosed in U.S. Pat. No. 5,773,423, are compounds of the formula (V):

wherein $X_1$ is $R^aR^bNC(\!\!=\!\!O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_2$ is selected from the group consisting of hydrogen, halo, $C_1$-$C_{10}$ alkyoxy, amino, $C_2$-$C_{10}$ alkenyl, and $C_2$-$C_{10}$ alkynyl; and $R_5$ is selected from the group consisting of R- and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo.

More specific A₃AR agonists include those of the above formula wherein $R^a$ and $R^b$ may be the same or different and are selected from the group consisting of hydrogen and $C_1$-$C_{10}$ alkyl, particularly when $R_2$ is hydrogen or halo, especially hydrogen.

Additional specific A₃AR agonists are those compounds wherein $R^a$ is hydrogen and $R_2$ is hydrogen, particularly when $R_5$ is unsubstituted benzyl.

More specific A₃AR agonists are such compounds wherein $R^b$ is a $C_1$-$C_{10}$ alkyl or $C_3$-$C_{10}$ cycloalkyl, particularly a $C_1$-$C_{10}$ alkyl, and more particularly methyl.

Especially specific are those A₃AR agonists where $R^a$ is hydrogen, $R^b$ is $C_1$-$C_{10}$ alkyl or $C_3$-$C_{10}$ cycloalkyl, and $R_5$ is R- or S-1-phenylethyl or a benzyl substituted in one or more positions with a substituent selected from the group consisting of halo, amino, acetamido, $C_1$-$C_{10}$ haloalkyl, and sulfo, where the sulfo derivative is a salt, such as a triethylammonium salt.

In addition, those compounds in which $R_2$ is a $C_2$-$C_{10}$ alkenylene of the formula $R^d$—C=C— where $R^d$ is a $C_1$-$C_8$ alkyl are also particularly noted in U.S. Pat. No. 5,773,423.

Also specific are those compounds wherein $R_2$ is other than hydrogen, particularly those wherein $R_2$ is halo, $C_1$-$C_{10}$ alkylamino, or $C_1$-$C_{10}$ alkylthio, and, more preferably, when additionally $R^a$ is hydrogen, $R^b$ is a $C_1$-$C_{10}$ alkyl, and/or $R_5$ is a substituted benzyl.

Further exemplary A₃AR agonists disclosed in U.S. Pat. No. 5,773,423 are modified xanthine-7-ribosides having the formula (VI):

wherein
X is O;
R$_6$ is R$^a$R$^b$NC(=O), wherein R$^a$ and R$^b$ may be the same or different and are selected from the group consisting of hydrogen, C$_1$-C$_{10}$ alkyl, amino, C$_1$-C$_{10}$ haloalkyl, C$_1$-C$_{10}$ aminoalkyl, and C$_3$-C$_{10}$ cycloalkyl;

R$_7$ and R$_8$ may be the same or different and are selected from the group consisting of C$_1$-C$_{10}$ alkyl, R- and S-1-phenylethyl, an unsubstituted benzyl group, and a benzyl group substituted in one or more positions with a substituent selected from the group consisting of C$_1$-C$_{10}$ alkyl, amino, halo, C$_1$-C$_{10}$ haloalkyl, nitro, hydroxy, acetamido, C$_1$-C$_{10}$ alkoxy, and sulfo; and R$_9$ is selected from the group consisting of halo, benzyl, phenyl, and C$_3$-C$_{10}$ cycloalkyl.

WO 99/06053 discloses in examples 19-33 compounds selected from:

N$^6$-(4-biphenyl-carbonylamino)-adenosine-5'-N-ethyluronamide;
N$^6$-(2,4-dichlorobenzyl-carbonylamino)-adenosine-5'-N-ethyluronamide;
N$^6$-(4-methoxyphenyl-carbonylamino)-adenosine-5'-N-ethyluronamide;
N$^6$-(4-chlorophenyl-carbonylamino)-adenosine-5'-N-ethyluronamide;
N$^6$-(phenyl-carbonylamino)-adenosine-5'-N-ethyluronamide;
N$^6$-(benzylcarbamoylamino)-adenosine-5'-N-ethyluronamide;
N$^6$-(4-sulfonamido-phenylcarbamoyl)-adenosine-5'-N-ethyluronamide;
N$^6$-(4-acetyl-phenylcarbamoyl)-adenosine-5'-N-ethyluronamide;
N$^6$—((R)-α-phenylethylcarbamoyl)-adenosine-5'-N-ethyluronamide;
N$^6$—((S)-α-phenylethylcarbamoyl)-adenosine-5'-N-ethyluronamide;
N$^6$-(5-methyl-isoxazol-3-yl-carbamoyl)-adenosine-5'-N-ethyluronamide;
N$^6$-(1,3,4-thiadiazol-2-yl-carbamoyl)-adenosine-5'-N-ethyluronamide;
N$^6$-(4-n-propoxy-phenylcarbamoyl)-adenosine-5'-N-ethyluronamide;
N$^6$-bis-(4-nitrophenylcarbamoyl)-adenosine-5'-N-ethyluronamide; and
N$^6$-bis-(5-chloro-pyridin-2-yl-carbamoyl)-adenosine-5'-N-ethyluronamide.

More specifically disclosed A3AR agonists which are to be used according to the present disclosure include:

2-chloro-N$^6$-(3-iodobenzyl)-9-[5-(methylamido)-β-D-ribofuranosyl]-adenine also known as 2-chloro-N$^6$-(3-iodobenzyl]-adenosine-5'-N-methyluronamide or by the abbreviation Cl-IB-IMECA;

N$^6$-(3-iodobenzyl)-2-methylamino-9-[5-(methylamido)-β-D-ribofuranosyl]-adenine, also known as N$^6$-(3-iodobenzyl)-adenosine-5'-N-methyluronamide or known as 1-Deoxy-1-[6-[[(3-iodophenyl)methyl]amino]-9H-purine-9-yl]-N-methyl-D-ribofuranuronamide or by the abbreviation IB-MECA;

N$^6$-2-(4-aminophenyl)ethyladenosine (APNEA);
N$^6$-(4-amino-3-iodobenzyl) adenosine-5'-(N-methyluronamide) (AB-MECA).

An example of an especially preferred A$_3$AR agonist is 2-Chloro-N$^6$-(3-iodobenzyl)-2-methylamino-9-[5-(methylamido)-β-D-ribofuranosyl]-adenine, also known as 2-Chloro-N$^6$-(3-iodobenzyl)-adenosine-5'-N-methyluronamide or by the abbreviation Cl-IB-MECA.

In some examples, Cl-IB-MECA is used for achieving a fat loss effect.

In one particular example, Cl-IB-MECA is used for treatment of obesity.

When referring to "A$_3$AR allosteric modulator" or "A$_3$ARM" it is to be understood as referring to the positive regulation, activation or increase of the receptor activity by binding of the allosteric modulator at the receptor's allosteric site which may be different from the binding site of the endogenous ligand or agonist thereof.

In one example, "modulation" denotes an effect of the A$_3$AR ligand on the receptor exhibited by an increase of at least 15% in the efficacy of the A$_3$ adenosine receptor by binding of the compound to the allosteric site of the receptor and/or by a decrease in dissociation rate of adenosine or an A$_3$AR agonist to the orthosteric binding site.

In one example, the modulation is by an A$_3$AR allosteric modulator (A$_3$ARAM) that is an imidazoquinoline derivative.

In one example, the A$_3$ARAM, or imidazoquinoline derivative has the following general formula (VII):

wherein:
R$_1$ represents an aryl or alkaryl being optionally substituted at the aromatic ring with one or more substituents selected from the group consisting of C$_1$-C$_{10}$ alkyl, halo, C$_1$-C$_{10}$ alkanol, hydroxyl, C$_1$-C$_{10}$ acyl, C$_1$-C$_{10}$ alkoxyl; C$_1$-C$_{10}$-alkoxycarbony, C$_1$-C$_{10}$ alkoxylalkyl; C$_1$-C$_{10}$ thioalkoxy; C$_1$-C$_{10}$ alkylether, amino, hydrazido, C$_1$-C$_{10}$ alkylamino, pyridylthio, C$_2$-C$_{10}$ alkenyl; C$_2$-C$_{10}$ alkynyl, thio, C$_1$-C$_{10}$ alkylthio, acetoamido, sulfonic acid; or said substituents can form together a cycloalkyl or cycloalkenyl fused to said aryl, the cycloalkyl or cycloalkenyl optionally comprising one or more heteroatoms; provided that said aryl is not an unsubstituted phenyl group;

R$_2$ represents hydrogen or a substituent selected from the group consisting of C$_1$-C$_{10}$ alkyl, C$_2$-C$_{10}$ alkenyl; C$_2$-C$_{10}$ alkynyl, C$_4$-C$_{10}$ cycloalkyl, C$_4$-C$_{10}$ cycloalkenyl, a five to seven membered heterocyclic aromatic ring, C$_5$-C$_{15}$ fused cycloalkyl, bicyclic aromatic or heteroaromatic rings; $C_1$-$C_{10}$ alkylether, amino, hydrazido, $C_1$-$C_{10}$ alkylamino, $C_1$-$C_{10}$ alkoxy, $C_1$-$C_{10}$-alkoxycarbony, $C_1$-$C_{10}$ alkanol, $C_1$-$C_{10}$ acyl, $C_1$-$C_{10}$ thioalkoxy, pyridylthio, thio, and $C_1$-$C_{10}$ alkylthio, acetoamido and sulfonic acid;

and pharmaceutically acceptable salts thereof.

According to some embodiments, the $R_1$ substituent in the $A_3$ARAM has the following general formula (VIII):

(VIII)

wherein n is 0 or an integer selected from 1-5; preferably, n is 0, 1 or 2; and $X_1$ and $X_2$ which may be the same or different, are selected from hydrogen halogen, alkyl, alkanol or alkoxy, indanyl, pyrroline provided that when said n is 0, $X_1$ and $X_2$ are not hydrogen.

In yet some further examples, $R_1$ in $A_3$ARAM is a substituent having the above formula (VIII), wherein $X_1$ or $X_2$, which may be the same or different, are selected from hydrogen, chloro, methoxy, methanol or a substituent having the formulae (VIIIa) or (VIIIb):

(VIIIa)

(VIIIb)

wherein Y is selected from N or CH.

In some yet further examples $R_2$ in $A_3$ARAM is selected from H, $C_{1-10}$ alkyl, $C_{4-10}$ cycloalkyl, the alkyl chain may be a straight or branched or form a four to seven membered cycloalkyl ring.

In one example, $R_2$ in $A_3$ARAM is selected from a five to seven membered heterocyclic aromatic ring.

In some examples, $R_2$ substituents in $A_3$ARAM are selected from H, n-pentyl, or a five membered heterocyclic aromatic ring having the following formula (IX):

(IX)

wherein Z is selected from O, S or NH, preferably O.

In accordance with one example, $R_2$ in the $A_3$ARAM comprises one or more fused rings, particularly so as to form bicyclic substituents.

Non-limiting examples of bicyclic compounds which may be used to form the substituents in the context of the $A_3$ARAM comprise bicyclo[2.2.1]heptane, bicyclo[4.1.0] heptane, bicyclo[4.1.0]heptan-3-carboxylic acid, bicyclo[3.1.0]hexan-3-carboxylic acid, bicyclo[4.1.0]heptan-2-carboxylic acid, bicyclo[3.1.0]hexan-2-carboxylic acid, and bicyclo[2.2.1]heptan-2-carboxylic acid.

In accordance with yet some other examples, $R_2$ in $A_3$ARAM is selected from 2-cyclohexene and 3-cyclohexene.

Specific imidazoquinoline derivatives which can be used as allosteric modulators of the $A_3$AR are listed below:

N-(4-Methyl-phenyl)-2-cyclopentyl-1H-imidazo[4,5-c]quinolin-4-amine

N-(4-Methoxy-phenyl)-2-cyclopentyl-1H-imidazo[4,5-c]quinolin-4-amine

N-(3,4-Dichloro-phenyl)-2-cyclopentyl-1H-imidazo[4,5-c]quinolin-4-amine

N-(4-Chloro-phenyl)-2-cyclopentyl-1H-imidazo[4,5-c]quinolin-4-amine

N-(3-Methanol-phenyl)-2-cyclopentyl-1H-imidazo[4,5-c]quinolin-4-amine

N-([3,4-c]Indan)-2-cyclopentyl-1H-imidazo[4,5-c]quinolin-4-amine

N-(1H-indazol-6-yl)-2-cyclopentyl-1H-imidazo[4,5-c]quinolin-4-amine

N-(4-Methoxy-benzyl)-2-cyclopentyl-1H-imidazo[4,5-c]quinolin-4-amine

N-(1H-Indol-6-yl)-2-cyclopentyl-1H-imidazo[4,5-c]quinolin-4-amine

N-(Benzyl)-2-cyclopentyl-1H-imidazo[4,5-c]quinolin-4-amine

N-(Phenylethyl)-2-cyclopentyl-1H-imidazo[4,5-c]quinolin-4-amine

N-(3,4-Dichloro-phenyl)-2-cycloheptyl-1H-imidazo[4,5-c]quinolin-4-amine

N-(3,4-Dichloro-phenyl)-2-furyl-1H-imidazo[4,5-c]quinolin-4-amine

N-(3,4-Dichloro-phenyl)-2-cyclobutyl-1H-imidazo[4,5-c]quinolin-4-amine

N-(3,4-Dichloro-phenyl)-2-cyclohexyl-1H-imidazo[4,5-c]quinolin-4-amine

N-(3,4-Dichloro-phenyl)-2-1H-imidazo[4,5-c]quinolin-4-amine

N-(3,4-Dichloro-phenyl)-2-pentyl-1H-imidazo[4,5-c]quinolin-4-amine.

The above imidazoquinoline derivatives are regarded as allosteric modulators as they were shown to have, on the one hand, reduced affinity, if any, to the orthosteric binding sites of the $A_1$ and $A_{2A}$, $A_{2B}$ adenosine receptors and reduced affinity to the orthosteric binding site of the $A_3$ adenosine receptor, and on the other hand, high affinity to the allosteric site of the $A_3$ adenosine receptor [International Patent Application No. WO07/089507, incorporated herein by reference].

A specifically preferred imidazoquinoline derivative in accordance with the present disclosure is N-(3,4-Dichlorophenyl)-2-cyclohexyl-1H-imidazo[4,5-c]quinolin-4-amine (also referred to at times by the abbreviation LUF6000 or CF602), being an $A_3$AR allosteric modulator.

In the context of the general formulae disclosed herein, the following meaning for the various terms is to be considered:

The term "alkyl" is used herein to refer to a linear or branched hydrocarbon chain having from 1 to 10 carbon atoms and more preferably 1 to 6 carbon atoms including, but not limited to, methyl, ethyl, n-propyl, isopropyl, n-butyl, t-butyl, n-heptyl, octyl and the like.

Similarly, the terms "alkenyl" and "alkynyl" denote a linear or branched hydrocarbon chain having, respectively, from 2 to 10, or from 3 to 10 carbon atoms and more preferably 2 to 6 or 3 to 6 carbon atoms, the alkenyl or alkynyl having at least one unsaturated bond.

The alkyl, alkenyl or alkynyl substituents may be substituted with a heteroatom containing group. Thus, it should be understood that while not explicitly stated, any of the alkyl modifications defined hereinabove and below, such as alkylthio, alkoxy, akanol, alkylamine etc, also include the corresponding alkenyl or alkynyl modifications, such as, akenylthio, akenyloxy, alkenol, alkenylamine, or respectively, akynylthio, alkynyloxy, alkynol, alkynylamine.

The term "aryl" denotes an unsaturated aromatic carbocyclic group of from 5 to 14 carbon atoms having a single ring (e. g., phenyl) or multiple condensed rings (e. g., naphthyl or anthryl). Preferred aryls include phenyl, indanyl, benzimidazole.

The term "alkaryl" refers to -alkylene-aryl groups preferably having from 1 to 10 carbon atoms in the alkylene moiety and from 6 to 14 carbon atoms in the aryl moiety. Such alkaryl groups are exemplified by benzyl, phenethyl and the like.

The term "Substituted aryl" refers to an aromatic moiety which is substituted with from 1 to 3 substituents as defined above. A variety of substituents are possible, as appreciated by those versed in the art. Nonetheless, some preferred substituents include, without being limited thereto, halogen, (substituted) amino, nitro, cyano, alkyl, alkoxy, acyloxy or alkanol, sulphonyl, sulphynyl.

The term "Halo" or "halogen" refers to fluoro, chloro, bromo and iodo, preferably to chloro.

The term "acyl" refers to the groups H—C(O)— as well as alkyl-C(O)—.

The term "alkanol" refers to the group —COH as well as alk-OH, "alk" denoting an alkylene, alkenylene or alkynylene chain.

The term "alkoxy" is used herein to mean —O-alkyl, including, but not limited to, methoxy, ethoxy, propoxy, isopropoxy, n-butoxy and the like.

The term "alkylthio" is used herein to mean —S-alkyl, including, but not limited to, methylthio, ethylthio, n-propylthio, isopropylthio, n-butylthio and the like.

The term "alkoxyalkyl" is used herein to mean -alkyl-O-alkyl, including, but not limited to, methoxymethyl, ethoxymethyl, n-propoxymethyl, isopropoxymethyl, n-butoxymethyl, isobutoxymethyl, t-butoxymethyl and the like.

The term "cycloalkyl" is used herein to mean cyclic hydrocarbon radicals including, but not limited to, cyclopropyl, cyclobutyl, cyclopentyl, cyclohexyl, cycloheptyl and the like.

The term "alkoxycarbonyl" is used herein to mean —C(O)O-alkyl, including, but not limited to, methoxycarbonyl, ethoxycarbonyl, propoxycarbonyl and the like.

The term "fused cycloalkyl" is used herein to mean any compound or substituent comprising at least two aliphatic rings which are connected at a single atom (to form a spirocyclic moiety), at two mutually bonded atoms or across a sequence of atoms (bridgehead). The fused rings may include any bicyclic, tricyclic as well as polycyclic moieties. Bicyclic substituents are preferred in accordance with some embodiments of the present disclosure.

The present disclosure also makes use of physiologically acceptable salts of an $A_3AR$ selective ligand, such as the above described compounds. A "physiologically acceptable salt" refers to any non-toxic alkali metal, alkaline earth metal, and ammonium salt commonly used in the pharmaceutical industry, including the sodium, potassium, lithium, calcium, magnesium, barium ammonium and protamine zinc salts, which are prepared by methods known in the art. The term also includes non-toxic acid addition salts, which are generally prepared by reacting the ligand with a suitable organic or inorganic acid. The acid addition salts are those which retain the biological effectiveness and qualitative properties of the free bases and which are not toxic or otherwise undesirable. Examples include, inter alia, acids derived from mineral acids, hydrochloric, hydrobromic, sulfuric, nitric, phosphoric, metaphosphoric and the like. Organic acids include, inter alia, tartaric, acetic, propionic, citric, malic, malonic, lactic, fumaric, benzoic, cinnamic, mandelic, glycolic, gluconic, pyruvic, succinic salicylic and arylsulphonic, e.g. p-toluenesulphonic, acids.

The $A_3AR$ ligand can be administered in a single dose (one time medication) or as a continuous treatment, for over a period of days, weeks or even months.

In one example, the $A_3AR$ ligand is used for long term treatment (chronic treatment and/or treatment of a chronic condition).

In the context of the present disclosure, long term treatment is to be understood to encompass a treatment window lasting for at least days, weeks, or months, until, for example, a sufficient fat loss is exhibited by parameters well known to any physician.

Further in the context of some examples of the present disclosure long term treatment encompasses chronic treatment, e.g. long term daily administration at times even without an envisaged end point for the treatment. In some examples, the long term treatment comprises at least one week of daily administration of the $A_3AR$ ligand, at times, one month daily treatment, at times, at least 2, 3, 4, 5, 6, or even 12 months of daily administration of the ligand.

When referring to "treatment" by the $A_3AR$ ligand it is to be understood to refer to any desired pharmacological and physiological effect that leads to medically significant improvement in the subject's well being as determined by parameters known in the world of obesity. For example, an improvement can be determined by a decrease in at least 1%, at times 5% in the level of total body mass or the level of the body fat mass of the subject.

In some examples, treatment is of a subject that is defined as suffering from a condition associated with excess peripheral fat accumulation, e.g. excess of adipose tissues.

In some examples, the treatment is in fact preventative treatment, for subjects in predisposition or tendency of gaining weight. At times, the treatment with A3AR ligand can be subsequent to or in combination with another treatment known to cause (e.g. as a side effect) increase in body mass.

The $A_3AR$ ligand can be administered on a daily basis or with a day or more intervals between administrations. In one embodiment, $A_3AR$ ligand is used on a daily basis, for chronic treatment.

The $A_3AR$ ligand can be administered systemically or locally. To this end, the $A_3AR$ ligand is combined with pharmaceutically acceptable carries to form a pharmaceutical composition suitable for a specific mode of administration and comprising an effective amount of the $A_3AR$ ligand.

By the term "pharmaceutically acceptable carrier" it is meant any one of inert, non-toxic materials, which do not react with the $A_3AR$ ligand and which can be added to the ligand to facilitate its delivery to subject.

In one embodiment, the carrier is one that is acceptable for preparation of a unit dosage form for oral administration.

An oral formulation may be in the form of a pill, capsule, in the form of syrup, emulsion, an aromatic powder, and other various forms. The carrier is selected at times based on the desired form of the formulation. The carrier may also at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. The carriers may be any of those conventionally used and is limited only by chemical-physical considerations, such as solubility and lack of reactivity with the $A_3AR$ ligand, and by the route of administration. The carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way.

Typical examples of carriers suitable for oral administration comprise (a) suspensions or emulsions in an appropriate liquid such as Cremophor RH40, or methylcellulose (e.g. Methocel A4M Premium); (b) capsules (e.g. the ordinary hard- or soft-shelled gelatin type containing, for example, surfactants, lubricants, and inert fillers), tablets, lozenges (wherein the active substance is in a flavor, such as sucrose and acacia or tragacanth or the active substance is in an inert base, such as gelatin and glycerin), and troches, each containing a predetermined amount of the tragacanth as solids or granules; (c) powders; (d) solution, typically when combined with a solubilizing enhancing agent; (e) liposome formulation; and others.

The $A_3AR$ ligand is used in an amount effective to achieve at least one fat loss effect. The "effective amount" can be readily determined, in accordance with the present disclosure, by administering to a plurality of tested subjects various amounts of the $A_3AR$ ligand and then plotting the response (for example combining several beneficial effects) as a function of the amount. At times, the amount to be used may depend on a variety of factors such as mode of administration, age, weight, body surface area, gender, health condition and genetic factors of the subject; other administered drugs; etc.

The effective amount of the $A_3AR$ ligand can be defined by a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

When the $A_3AR$ ligand is an $A_3AR$ agonist, the effective amount may, for example, be an amount of at least about 10 mg/day, e.g. at least about 10 mg in a treatment regime of once daily treatment, at least about 5 mg twice daily, at least about 3.3 mg thrice daily, etc.).

A dose of at least about 10 mg/day may be a dose of at least about 15 mg/day, at least about 20 g/day, at least about 25 mg/day. In some embodiments, the dose is 25±5 mg/day.

The total amount of $A_3AR$ ligand given a day to a patient, irrespective of the number of administrations is referred to herein as a "daily treatment dose".

Thus, in one example, the $A_3AR$ ligand is formulated in a unit dosage form for administering of the daily treatment dose of at least 10 mg/day. Where the dosage form is intended for administering to a subject in a treatment regimen comprising n doses per day, then a unit dosage form may comprise 1/n portion of the daily treatment dose (e.g., where the intended daily treatment dose is 20 mg and the treatment regimen is twice daily then each unit dosage form will have a dose of 10 mg; or where the intended daily treatment dose is 25 mg and the treatment regimen is twice daily then each unit dosage form will have a dose of 12.5 mg).

In some examples, the $A_3AR$ ligand is administered in combination with anti-obesity treatment. In the context of the present disclosure, anti-obesity treatment can include any treatment known in the art including eating plan and special diets, physical activity plan, treatment with a medicament, bariatric surgery, weight loss devices.

In some example, $A_3AR$ ligand is used in combination with a commercially available and medicinally acceptable weight loss medicine. Examples of commercially available and FDA approved medicaments include Orlistat (Alli, Xenical), Lorcaserin (Belviq), Phentermine and Topiramate (Qsymia), Bupropion and Naltrexone (Contrave), Liraglutide (Saxenda, Victoza).

It is to be appreciated that treatment is to be considered effective if in a subject diagnosed to have obesity or have a body mass index (BMI) of 30 or higher, there is at least a weigh loss of at least 3%, at times at least 4% or at least 5% of the total weight as compared to the weight before treatment begun. In some examples, an effective treatment is one where there is a weight loss of at least between 3% to 6% or between 5% to 10% of the total weight before treatment begun.

As used herein, the forms "a", "an" and "the" include singular as well as plural references unless the context clearly dictates otherwise. For example, the term "an $A_3AR$ ligand" includes one or more compounds which are capable of specifically affecting, directly or indirectly, fully or partially, the activity of the $A_3AR$.

Further, as used herein, the term "comprising" is intended to mean that the composition include the recited active agent, i.e. $A_3AR$ ligand, but not excluding other elements, such as physiologically acceptable carriers and excipients as well as other active agents. The term "consisting essentially of" is used to define compositions which include the recited elements but exclude other elements that may have an essential significance on any one of the fat loss effects. "Consisting of" shall thus mean excluding more than trace elements of other elements. Embodiments defined by each of these transition terms are within the scope of this invention.

Further, all numerical values, e.g. when referring the amounts or ranges of the elements constituting the composition comprising the $A_3AR$ ligand as an active ingredient, are approximations which are varied (+) or (−) by up to 20%, at times by up to 10% of from the stated values. It is to be understood, even if not always explicitly stated that all numerical designations are preceded by the term "about".

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

NON-LIMITING EXAMPLES

Example 1—CF 102 Effect on the Proliferation of 3T3-L1 Adipocytes

3T3-L1 pre-adipocytes were purchased from American Type Culture Collection (ATCC; Manassas, VA, USA). The pre-adipocytes were maintained in Dulbecco's modified Eagle's medium (DMEM; Hyclone, South Logan, UT, USA), and supplemented with 10% newborn calf serum (Hyclone) and antibiotics (Hyclone) at 37° C. in 5% $CO_2$.

To induce adipocyte differentiation, the pre-adipocytes were plated at 24-well plates. After confluence, the medium was changed and 10 μg/ml insulin, 1 μM DEX and 0.5 mM IBMX was added. Two days later the media were changed to the basal medium supplemented with 10% FBS and 10 μg/ml insulin. The media were replaced every 2 days for a period of 8-14 days.

To evaluate cell proliferation, $^3$H-thymidine incorporation assay was used. The 3T3-L1 cells (5,000 cells/well) were incubated with 5 or 10 nM CF102 96-well plate for 48 hours. Each well was pulsed with 1 mCi $^3$H-thymidine for the last 24 hours. Cells were harvested and the $^3$H-thymidine uptake was determined in an LKB liquid scintillation counter (LKB, Piscataway, NJ, USA).

Results:

FIG. 1 depicts the dose dependent inhibitory effect of CF102 on the proliferation of the 3T3-L1 adipocytes. The adipocyte cells that were incubated with CF102 5 nM and 10 nM exhibited reduction of more than 20% and 40%, respectively, compared to the control measurement.

Example 2—CF102 Effect on Lipid Production in 3T3-L1 Adipocytes

Pre-adipocytes were incubated in a differentiated medium (DMEM high glucose+10% FBS) containing 10 μg/ml insulin, 1 μM DEX and 0.5 mM IBMX and treated with 5 nM CF102 for 48 h to evaluate its potential anti-adipogenic effect.

The accumulation of lipid droplets was evaluated by staining with Oil-Red-O. Briefly, cells were washed with PBS, incubated with 3.7% HCHO for 1 hr and then, incubated with Oil-Red-O solution for 45 min. Cells were washed very well to remove the excess of Oil-Red-O, visualized and photographed under an Olympus microscope with a Leica camera. For the quantification of lipid accumulation, cells were dissolved in isopropanol and the optical density was read on a Dynatech Corp. Microelisa reader (Chantilly, VA) at 595 nm. The degree accumulation of lipid droplets was proportional to the optical density.

The accumulation of lipid droplets was visualized under a microscope and can be seen in FIGS. 2A-2B, where FIG. 2A shows a microscopic image of the control measurement and FIG. 2B shows a microscopic image of lipid droplet derived from pre-adipocytes treated with 5 nM of CF102.

Results:

FIG. 3 depicts the inhibition in lipid accumulation of cells pre-exposed to 5 nM CF102. Data are expressed as OD value at 595 nm in the vehicle treated (control) vs. CF102 treated group. (p=0.01).

Example 3—CF102 Effect on Weight in High Fat Diet (HFD) Mice Vs. Mice Fed with Regular Diet Because complications from obesity such as diabetes and cardiovascular disease usually require decades, surrogate animal models are important for studying the molecular aspects of obesity and its pathophysiological effects. One of these models that are gaining increasing attention is the diet-induced obesity model in mouse. The present protocol is designed to evaluate effects of CF102 in an in vivo mouse model of Diet-Induced obesity.

Mice

The mice utilized are C57BL/6J males, 4-6 weeks old (The Jackson Laboratory, stock 000664).

Diet 60 kcal % fat diet (Research Diets, D12492i)

CF102 Treatments

Two types of treatment, preventive and therapeutic will be investigated.

Experimental Design:

Group I-II: Naïve animals (n=20) were fed with a regular diet, served as a control group and were defined as 'Lean Diet' After 12 weeks, mice were divided into 2 groups (n=10 per group), the first was treated with a daily oral administration of CF102 (Can-Fite BioPharma, Cat #A14402-10; 100 μg/Kg) for 4 weeks and the second with vehicle only.

Group III-IV—Naïve mice (n=20) were fed with HFD for 12 weeks. After 12 weeks, mice were divided into 2 groups (n=10 per group), the first was treated with daily oral administration of CF102 (Can-Fite BioPharma, Cat #A14402-10; 100 μg/Kg) for 4 weeks and the second with vehicle only.

Results and Analysis

In the Lean diet group, CF102 caused weight loss in the animals as compared to control.

Figure 4A:
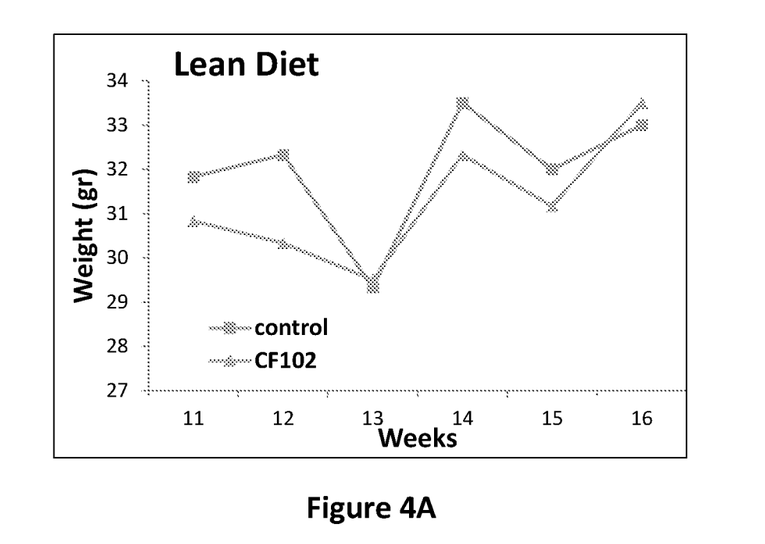
FIGS. 4A-4B show the change in mice weight fed with regular diet all along the study period. On week 12 treatment with CF102 or vehicle was initiated (FIG. 4A) or change in mice weight fed with high fat diet (HFD) all along the study period. On week 12 treatment with CF102 or vehicle was initiated (FIG. 4B)
Figure 4B:
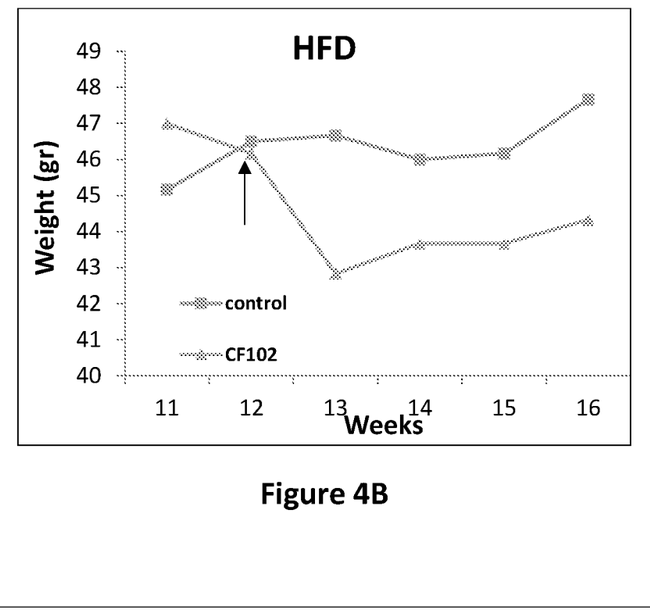

Specifically, FIG. 4A shows that naïve mice under Lean diet treated with CF102 did not exhibit any weight loss as compared to untreated naïve mice. However, as shown in FIG. 4B, mice under HFD, exhibited a significant (p<0.001) weight loss effect upon treatment with CF102 (arrow indicates point of treatment initiation).

Example 4—Effect of CF602, an A3AR Allosteric Modulator, on Body Weight of Diabetic Rats Diabetes is one of the complications of obesity. Therefore, the effect of an $A_3AR$ ligand on body weight in a diabetic model was also evaluated.

Methods:

Sprague Dawley male rats (8-10 week old) were administered IP with Streptozotocin (STZ) at a dose level of 60 mg/kg in citrate buffer to create a diabetic model. Only animals with blood glucose level higher than 250 mg/dL were included in the study. CF602, an allosteric A3AR ligand was administered orally twice daily for five days at a dose of 100 μg/kg. Body weight was monitored after 5 days.

Figure 5:
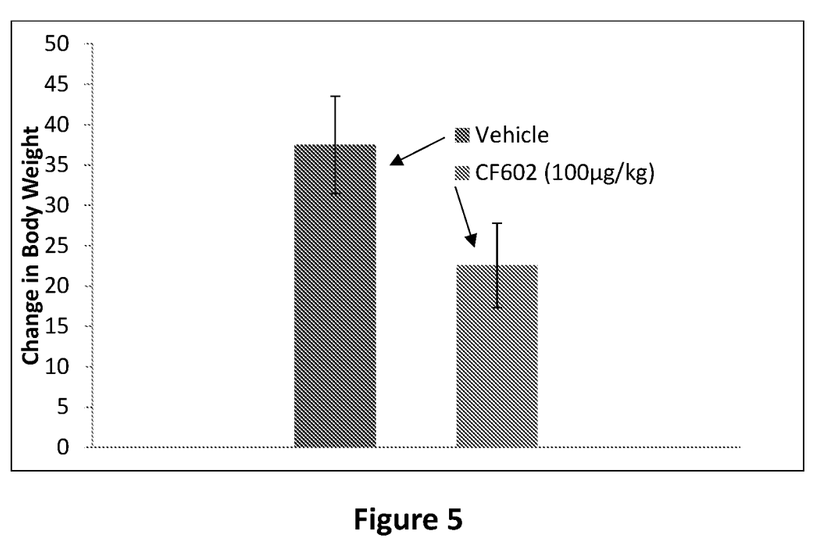
FIG. 5 is a graph showing the effect of the $A_3AR$ allosteric modulator, CF602, on body weight in an experimental rat model of diabetes induced by STZ.

Results:

FIG. 5 shows the weight change from baseline, namely weight at the end of treatment minus weight before treatment (i.e. the difference). The weight loss was significant (p<0.03) decrease in body weight in the CF602 treated animals.

The invention claimed is:

1. A method for treating a subject comprising administering to said subject an amount of an $A_3$ adenosine receptor ($A_3AR$) ligand, the amount being effective to achieve at least one fat loss effect selected from:
   reduce weight of the subject;
   reduce body fat mass in the subject
   wherein said fat loss effect refers to reducing adipose tissues that are intended to store fat and excluding ectopic fat,
   wherein said $A_3AR$ ligand inhibits adipocyte proliferation, and
   wherein said $A_3AR$ ligand is Cl-IB-MECA or N-(3,4-Dichloro-phenyl)-2-cyclohexyl-1H-imidazo [4,5-c] quinolin-4-amine (CF602).

2. The method according to claim 1, wherein said ligand is in a dosage form suitable for daily administration to said subject.

3. The method according to claim 2, wherein said dosage form is suitable for administration once or twice a day.

4. The method according to claim 1, wherein said ligand is in a dosage form suitable for oral administration.

5. The method according to claim 1, wherein said $A_3AR$ ligand is administered in combination with an anti-obesity treatment.

* * * * *